United States Patent
Sun et al.

(10) Patent No.: US 8,624,005 B2
(45) Date of Patent: Jan. 7, 2014

(54) METHOD OF PROTEIN REFOLDING WITH ION EXCHANGE RESINS AND THE APPLICATION OF THE SAME

(75) Inventors: Yan Sun, Tianjin (CN); Guozhen Wang, Tianjin (CN); Qinghong Shi, Tianjin (CN); Xiaoyan Dong, Tianjin (CN)

(73) Assignee: Tianjin University, Tianjin (CN)

( * ) Notice: Subject to any disclaimer, the term of this patent is extended or adjusted under 35 U.S.C. 154(b) by 0 days.

(21) Appl. No.: 13/642,414

(22) PCT Filed: Jun. 30, 2011

(86) PCT No.: PCT/CN2011/001075
§ 371 (c)(1),
(2), (4) Date: Oct. 19, 2012

(87) PCT Pub. No.: WO2012/048514
PCT Pub. Date: Apr. 19, 2012

(65) Prior Publication Data
US 2013/0060007 A1      Mar. 7, 2013

(30) Foreign Application Priority Data
Oct. 14, 2010 (CN) .......................... 2010 1 0507365

(51) Int. Cl.
- *C07K 1/00* (2006.01)
- *C07K 14/00* (2006.01)
- *C07K 16/00* (2006.01)
- *C07K 17/00* (2006.01)
- *A23J 1/00* (2006.01)

(52) U.S. Cl.
USPC ......................................... 530/416; 530/412

(58) Field of Classification Search
USPC ....................................................... 530/416
See application file for complete search history.

(56) References Cited

PUBLICATIONS

Inglezakis, V. et al. "Pretreatment of Natural Clinoptilolite in a Laboratory Sacle Ion Exchange Packed Bed" (2001) Wat. Res. 35 2161-2166.*
Vincentelli, R. et al. "High—throughput automated refolding screening of inclusion bodies" Protein Science (2004) 13:2782-2792.*
Trivedi, V. et al "Co-refolding denatured—reduced hen egg white lysozyme with acidic and basic proteins" FEBS Letters 418 (1997) 363-366.*
Clark, E. "Refolding of Recombinant Proteins" Current Opinion in Biotechnology (1998) 9:157-163.*
Wang, Chaozhan et al, "Refolding of Denatured/Reduced Lysozyme at High Concentrations by Artificial Molecular Chaperone—Ion Exchange Chromatography," *Biotechnology. Progress.*, Mar. 1, 2010, vol. 26, No. 4, pp. 1073-1079.
Trivedi, V.D. et al, "Co-refolding Denatured—Reduced Hen Egg White Lysozyme with Acidic and Basic Proteins," *FEBS Letters*, 1997, vol. 418 , pp. 363-366.
Chen, Yu, et al, "Adsorptive Refolding of a Highly Disulfide—Bonded Inclusion Body Protein using Anion—Exchange Chromatography," *Journal of Chromatography A*, vol. 1216, Apr. 18 2009, pp. 4877-4886.
Sep. 22, 2011 International Search Report issued in Application No. PCT/CN2011/001075.

* cited by examiner

*Primary Examiner* — John S Brusca
*Assistant Examiner* — Gerard Lacourciere
(74) *Attorney, Agent, or Firm* — Oliff & Berridge, PLC

(57) ABSTRACT

A method for protein refolding with an ion exchange resin. The method includes (a) choosing an ion exchange resin that having charged groups with the same sign as a net charge of a denatured protein to be refolded; (b) removing heterogeneous ions from the ion exchange resin by washing the ion exchange resin sequentially with saline solution and deionized water, to prepare the ion exchange resin; (c) mixing the ion exchange resin with a refolding buffer thoroughly, then adding the denatured protein to the refolding buffer and allowing the denatured protein to refold; and then (d) collecting the supernatant by centrifugation or settlement, to obtain a solution containing the refolded protein.

10 Claims, 5 Drawing Sheets

METHOD OF PROTEIN REFOLDING WITH ION EXCHANGE RESINS AND THE APPLICATION OF THE SAME

This is a U.S. National Phase of International Application No. PCT/CN2011/001075, filed Jun. 30, 2011, which in turn claims the benefit of Chinese Patent Application No. 201010507365.5, filed Oct. 14, 2010. The disclosure of the prior applications is hereby incorporated by reference herein in its entirety.

BACKGROUND OF THE INVENTION

1. Field of the Invention

The present invention relates to a protein refolding method, in particular, relates to the method of protein refolding with ion exchange resins and the application of the same. The invention belongs to the technical field of protein refolding in biotechnology.

2. Description of the Related Art

Since the advent of recombinant DNA technology in the early 1970s, the rapid development of biotechnology has greatly propelled the mass production of recombinant proteins. To produce a recombinant protein, Escherichia coli (E. coli) is usually the preferred choice as the host because it has many advantages, such as simple plasmid construct, low nutrient requirement, fast growth, high level of expression, and ease of separation. Many of the over-expressed target proteins accumulate as inclusion body in E. coli. The inclusion body has correct primary structure but no high-level structure. Thus, it has no biological activity and has to be refolded to achieve its native bioactivity. Because of the complicated protein structure, refolding is a difficult technology during the production of biological pharmaceutical proteins in the gene project. A major challenge in protein refolding is the aggregation of folding intermediates, which is parallel to the on-pathway folding method and is the leading cause of low refolding yield. Therefore, the inhibition of the aggregation is the great challenge for protein refolding in industrial production.

One strategy to inhibit the formation of the aggregation is to use folding additives in the refolding system. However, additive-assisted methods bring the trouble of further separation due to the presence of additives, and most of folding additives are not reusable. Moreover, protein chaperones are too expensive for industrial applications.

On-column refolding by chromatography is another approach to inhibiting aggregation of folding intermediates. But there is no report about the method for protein refolding with ion exchange resins as an additive. Protein refolding by chromatography is usually carried out in two modes, flow-through mode (size exclusion chromatography) and adsorptive mode (hydrophobic interaction chromatography, ion-exchange chromatography, and affinity chromatography). Unfolded proteins are adsorbed in the chromatographic columns by hydrophobic interactions, electrostatic interactions, or specific affinity and thus hydrophobic interaction between protein molecules can effectively be inhibited. However, chromatography is low throughput, facilities of chromatography are rather expensive and need high-cost maintenance, columns are prone to blockage by protein aggregation, high-quality degassed and filtrated mobile phases are needed, and operation is relatively complex. In addition to these problems, it is usually difficult to achieve refolding products with high concentrations by the on-column method. So far, no application of ion exchange resins with the same sign of charge as the proteins to be refolded has been reported for protein refolding.

To overcome the drawbacks of refolding with additives and chromatography, the present invention provides a method for protein refolding with the ion exchange resins as an additive. The method provided has several advantages over other methods for protein refolding including no requirement for chromatographic facilities, simple operation and no additional contaminant introduced during the process of refolding. Finally, the ion exchange resins can be recycled via solid-liquid separation and regeneration.

SUMMARY OF INVENTION

The invention introduces a method for efficient refolding of proteins by suppressing protein aggregation. In the present invention, it is achieved by electrostatic repulsion between the unfolded protein and/or folding intermediates and ion exchange resins carrying like-charged groups with the protein to be refolded. The method provided herein has several advantages over other methods for protein refolding including no requirement for chromatographic facilities, simple operation and no additional contaminant introduced during the process of refolding. Finally, the ion exchange resins can be recycled via solid-liquid separation and regeneration.

To achieve the purpose, the invention provides a method for protein refolding with the ion exchange resin as an additive, comprising:

a. choosing an ion exchange resin that is like-charged with the protein to be refolded.

b. removing heterogeneous ions by washing sequentially with saline solution and deionized water, in order to prepare the ion exchange resin.

c. mixing said ion exchange resin with the refolding buffer thoroughly; and then adding the denatured protein to the refolding buffer for refolding.

d. after refolding, collecting the supernatant by centrifugation or settlement, in order to achieve the refolded protein solution.

The method, wherein said ion exchange resin is the positively charged anion-exchange resin or the negatively charged cation-exchange resin.

The method, wherein said positively charged anion-exchange resin is DEAE-Sepharose Fast Flow or Q-Sepharose Fast Flow.

The method, wherein said negatively charged cation-exchange resin is SP-Sepharose Fast Flow or CM-Sepharose Fast Flow.

The method, wherein said refolding buffer contains 0.02-0.1 mol/L Tris, 0-0.003 mol/L ethylenediaminetetraacetic acid disodium (EDTA-$Na_2$), and 0-2 mol/L urea, and the pH value of said refolding buffer is 7.5-9.0.

The method, wherein said refolding buffer contains inorganic salt and the concentration thereof is no higher than 0.05 mol/L.

The method, wherein the step b further comprises the following sub-steps: firstly, transferring the ion exchange resin into a sintered glass filter funnel so as to drain the liquid by suction; then washing the said resin 3-8 times successively with 0.2-2 mol/L NaCl solution and deionized water; the volume of NaCl solution and deionized water in each washing cycle is 20-30 times as that of the resin.

The method, wherein in step c, the concentration of said ion exchange resin in the refolding buffer is 0.025-0.5 g/ml; the mixture is put in the thermostatic water bath at a temperature of 20-37° C., and shaken to be pre-equilibrated until the temperature of the mixture is stable; then the protein to be refolded is added, and the final concentration of the protein in the refolding buffer is 0.07-4 mg/ml; after being thoroughly mixed, the mixture is put into the thermostatic water bath and shaken at 50-170 rpm for refolding, wherein, the temperature for refolding is the same as that for pre-equilibration.

An application of the method, wherein, the method can be applied to the refolding of aggregation-prone proteins, including the proteins without disulfide bonds, and the proteins with disulfide bonds that are not reduced or incorrectly matched, in addition to the proteins with disulfide bonds that are reduced or incorrectly matched.

According to the present invention, the method for protein refolding with the ion exchange resin as a refolding additive was generally accomplished as follows. An ion exchange resin, which is like-charged with that of the protein to be refolded at the refolding pH, was used in the protein refolding. After the resin was drained in a sintered glass filter funnel, the resin was washed 3-8 times with 0.2-2 mol/L NaCl and then washed 3-8 times with deionized water. In each washing cycle, the volume of NaCl solution and deionized water was 20-30 times as that of the settled resin. Then the ion exchange resins processed was transferred into the refolding buffer containing 0.02-0.1 mol/L Tris, 0-0.003 mol/L EDTA-$Na_2$, 0-2.0 mol/L urea, and having a pH value between 7.5 and 9.0. The concentration of the ion exchange resins in the suspension was 0.025-0.5 g/ml. The suspension was incubated in a thermostatic water bath and pre-equilibrated until the temperature of the suspension is stable. The temperature of thermostatic water bath ranged from 20° C. to 37° C. Then, the reduced and denatured protein to be refolded was mixed with the suspension. The final protein concentration in the refolding buffer ranged from 0.07 mg/ml to 4.0 mg/ml. After mixing thoroughly, the mixture was transferred and shaken in the thermostatic water bath at 50-170 rpm, and the temperature for refolding was the same as that for pre-equilibration of the refolding buffer. After that, the supernatant was collected by centrifugation or gravity settlement, and the settled ion exchange resin was further washed 3-5 times with washing buffer. The washing buffer was the refolding buffer, and in each washing cycle, the volume of the refolding buffer used was 1.5 to 3 times as that of the settled ion exchange resin. After washing, the supernatant was collected by centrifugation or gravity settlement, and the collected supernatant was pooled to achieve refolded protein solution. Furthermore, the ion exchange resin could be recycled by washing successively with 0.5-2 mol/L NaCl solution and deionized water.

The present method for protein refolding with a like-charged ion exchange resin can be applied to refolding of proteins at high concentration. It can also be applied to the refolding of aggregation-prone proteins.

The method can be used to facilitate refolding of proteins with or without disulfide bond. For proteins without disulfide bond, the pH value of refolding solution can be deviated from the isoelectric point by more than 1.0. For proteins with reduced disulfide bond, a preferred pH value is deviated from the isoelectric point by more than 1.0, but no lower than 7.5.

The method of the invention can be used with urea in the refolding buffer to facilitate folding cooperatively, since the anti-aggregation effect of like-charged ion exchange resins and urea are synergetic.

There are four key techniques in the invention. Firstly, it refers to the selection of an ion exchange resin: selecting an ion exchange resin that is like-charged with the protein to be refolded, and the charge repulsion between the ion exchange resin and protein can inhibit aggregation effectively; secondly, it refers to the preparation of the resin: washing with sodium chloride solution to remove heterogeneous ions, and then washing with deionized water to remove salt so as to avoid weakening of the electrostatic interaction between a protein and the ion exchange resin in the course of protein refolding; thirdly, it refers to the order of adding the ion exchange resin and the denatured protein into refolding buffer: the ion exchange resin should be added before the denatured protein because the aggregation of protein is the most serious at the initial stage of refolding; finally, it refers to the recycling of the ion exchange resin after refolding: in virtual of the charge repulsion between the protein and the resin, protein separation can be achieved by centrifugation or settlement and the resin can be recycled.

Compared with other chromatographic technologies in protein refolding, this invention for using an ion exchange resin that is like-charged with the protein to be refolded as an additive in protein refolding has the advantages described as bellow: (1) the ion exchange resin used as the addictive is insoluble so that it may prevent protein from being contaminated; (2) it is easy to separate the resin from the protein mixture by gravity settlement or centrifugation after protein refolding; (3) the invention requires no expensive chromatographic facilities, and thus, it is easy to operate at a low cost and suitable for large scale production.

DETAILED DESCRIPTION OF THE EMBODIMENTS

Figure 1:
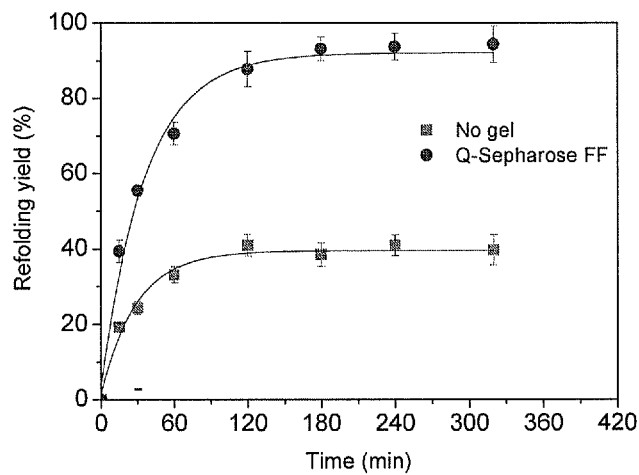
FIG. 1 illustrates the strong anion-exchange resin, Q-Sepharose Fast Flow (Q-Sepharose FF), facilitates refolding of denatured and reduced lysozyme at 4 mg/ml.

The following examples are included to demonstrate the certain aspects and embodiments of the present invention.

Example 1

Strong anion-exchange resin, Q-Sepharose Fast Flow, facilitates the refolding of the denatured and reduced lysozyme at 4 mg/ml.

Ion-Exchange Resin Preparation

As lysozyme carries positive charges at pH 8.5, a positively charged anion-exchange resin was chosen, such as Q-Sepharose Fast Flow. After 2 ml of the resin stored in ethanol solution with a concentration of 20% was placed in a sintered glass filter funnel, 20% of the ethanol solution was drained by suction, and then the resin was washed four times with 160 ml NaCl solution with a concentration of 0.5 mol/L. In each washing cycle, 40 ml of the said NaCl solution was added, and the mixture was stirred thoroughly with a glass stick; after that, the solution was drained by suction. The resin was further washed five times with 200 ml deionized water, and in each of these washing cycles, 40 ml of deionized water was added and the mixture was stirred thoroughly; then the solution was drained by suction; finally, the resin was washed with deionized water, and the water solution was drained by suction for 10 minutes and then the resin was stored in a refrigerator at 4° C.

Preparation of Denatured and Reduced Protein

In preparation of the denatured and reduced protein, 60 mg/ml lysozyme in denatured and reduced buffer containing 8 mol/L urea, 0.1 mol/L DTT, 0.001 mol/L EDTA-$Na_2$ and 0.1 mol/L Tris-HCl (pH 8.5) was incubated at 40° C. for 3 hours. The refolding buffer was 0.1 mol/L Tris-HCl buffer at a pH of 8.5, containing 1.0 mol/L urea, 0.0054 mol/L cystamine, and 0.001 mol/L EDTA-$Na_2$. In the absence of the resin, the refolding buffer was incubated at 20° C. until the temperature of the buffer stable. In the presence of the resin, 0.2 g of the resin was added into the refolding buffer to prepare 1.0 ml of the mixture, and then the mixture was incubated at 20° C. until the temperature of the mixture stable. Then, the denatured protein was added to the above refolding buffer, and thoroughly mixed. After that, the mixture was put on the thermostatic shaking bed for refolding at 20° C. and 170 rpm.

Activity Assay

Lysozyme activity was assayed with *Micrococcus lysodeikticus* as a substrate. In the assay, 1.30 ml of substrate in phosphate buffer (pH 6.2) with a concentration of 0.25 mg/ml was mixed thoroughly with 0.1 ml diluted protein refolding buffer, and the variation of absorbency of the reaction solution was measured at 450 nm. The assaying was conducted at a temperature of 25° C. The enzyme activity was calculated by the ratio of absorbance decrease in the initial 90 s of refolded lysozyme to that of native enzyme.

Refolded Protein Collection

After refolding, the supernatant was collected by centrifugation at 10000 rpm for 1 minute. Then, 0.4 ml refolding buffer was added to wash the settled resin, and the supernatant further obtained was collected by centrifugation. In order to make sure that the refolded protein was completely collected, the settled resin was washed four times finally. The pooled supernatant was used for further analysis.

Results

The variations of refolding yield in terms of time in the presence and absence of the anion-exchange resin are illustrated in FIG. 1. The result indicated that the application of the anion-exchange resin, Q-Sepharose Fast Flow, as the additive could significantly improve the refolding yield of denatured and reduced lysozyme that is positively charged. Even the protein concentration was 4 mg/ml, the refolding yield of lysozyme could also achieve 94%. However, the refolding yield of lysozyme was only 40% in the absence of the resin.

Recovery of the Ion Exchange Resin

After the refolding, 0.2 g Q Sepharose Fast Flow was equilibrated with 0.5 mol/L NaCl solution for 15 minutes, and then the mixture was centrifuged at 10000 rpm for 1 minute to remove adsorbed impurities in the supernatant. After that, the resin was transferred into a sintered glass filter funnel and washed four times with 16 ml NaCl solution at the concentration of 1 mol/L. Finally, the resin was further washed four times with 16 ml deionized water, and stored in ethanol solution with a concentration of 20%.

Example 2

Weak anion-exchange resin, DEAE-Sepharose Fast Flow, facilitates the refolding of denatured and reduced lysozyme at a protein concentration of 4 mg/ml.

Ion-Exchange Resin Preparation

As lysozyme carries positive charges at pH 8.5, a negatively charged anion-exchange resin was chosen, such as DEAE-Sepharose Fast Flow. After 2 ml such resin stored in ethanol solution with a concentration of 20% was placed in a sintered glass filter funnel, 20% of the ethanol solution was drained by suction, and then the resin was washed three times with 120 ml NaCl solution with a concentration of 2 mol/L. In each washing cycle, 40 ml of the said NaCl solution was added, and the mixture was stirred thoroughly with a glass stick; after that, the solution was drained by suction. The resin was further washed three times with 180 ml deionized water, and in each of these washing cycles, 60 ml deionized water was added and the mixture was stirred thoroughly; and then the solution was drained by suction; finally, the resin was washed with the deionized water, and was drained by suction for 10 minutes and then stored in a refrigerator at 4° C.

Preparation of Denatured and Reduced Protein

In preparation of denatured and reduced protein, 60 mg/ml lysozyme in denatured and reduced buffer containing 8 mol/L urea, 0.1 mol/L DTT, 0.001 mol/L EDTA-$Na_2$ and 0.1 mol/L Tris-HCl (pH 8.5) was incubated at 40° C. for 3 hours. The refolding buffer was 0.02 mol/L Tris-HCl buffer at a pH of 8.5, containing 1.0 mol/L urea, 0.0054 mol/L cystamine, and 0.003 mol/L EDTA-$Na_2$. In the absence of the resin, the refolding buffer was incubated at 37° C. until the temperature of the buffer stable. In the presence of the resin, 0.2 g of the resin was added into the refolding buffer to prepare 1.0 ml of the mixture, and then the mixture was incubated at 37° C. until the temperature of the mixture stable. Then, the denatured protein was added to the refolding buffer, and thoroughly mixed. Finally, the mixture was put on the thermostatic shaking bath for refolding at 37° C. and 50 rpm.

Activity Assay

Lysozyme activity was assayed with *Micrococcus lysodeikticus* as a substrate. In the assay, 1.30 ml of substrate in phosphate buffer (pH 6.2) with a concentration of 0.25 mg/ml was mixed thoroughly with 0.1 ml diluted protein refolding buffer, and the variation of absorbency of the reaction solution was measured at 450 nm. The assaying of the variation was conducted at a temperature of 25° C. The enzyme activity was calculated by the ratio of absorbance decrease in the initial 90 s of refolded lysozyme and that of native enzyme. In the method of refolding of the invention, the final concentration of the resin in the refolding was 0.2 g/ml.

Refolded Protein Collection

After refolding, the supernatant was collected by centrifugation at 10000 rpm for 1 minute. Then, 0.6 ml refolding buffer was added to wash the settled resin. After that, the supernatant further obtained was collected by centrifugation at 10000 rpm for 1 minute. In order to make sure that the refolded protein was completely collected, the settled resin was washed three times finally. The pooled supernatant was used for further analysis.

Results

Figure 2:
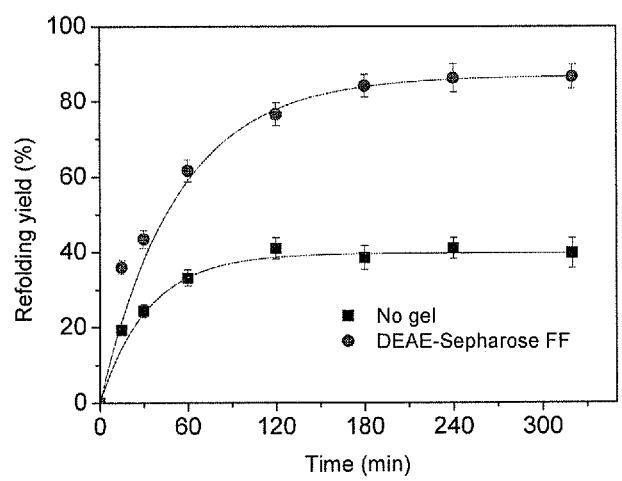
FIG. 2 illustrates the weak anion-exchange resin, DEAE-Sepharose Fast Flow (DEAE-Sepharose FF), facilitates refolding of denatured and reduced lysozyme at 4 mg/ml.

The variations of refolding yield in terms of time in the presence and absence of the anion-exchange resin are illustrated in FIG. 2. The result indicated that the application of the anion-exchange resin, such as DEAE-Sepharose Fast Flow, as the additive could significantly improve the refolding yield of denatured and reduced lysozyme. Even the protein concentration was 4 mg/ml, the refolding yield of lysozyme could also achieve 85%. However, the refolding yield of lysozyme was only 40% in the absence of the resin Recovery of Ion Exchange Resins After the refolding, DEAF Sepharose Fast Flow was equilibrated with 2 mol/L NaCl solution for 5 minutes, and then the mixture was centrifuged at 10000 rpm for 1 minute to remove adsorbed impurities in the supernatant. After that, the resin was transferred into a sintered glass filter funnel and washed three times with 16 ml NaCl solution at the concentration of 0.5 mol/L. Finally, the resin was further washed four times with 16 ml deionized water, and stored in ethanol solution with a concentration of 20%.

Example 3

Strong anion-exchange resin, Q-Sepharose Fast Flow, facilitates the refolding of the denatured and reduced lysozyme at 4 mg/ml, in the presence of NaCl.

Ion-Exchange Resin Preparation

The anion-exchange resin was the Q-Sepharose Fast Flow mentioned in EXAMPLE 1 of this invention.

Preparation of Denatured and Reduced Protein

In preparation of denatured and reduced protein, 60 mg/ml lysozyme in denatured and reduced buffer containing 8 mol/L urea, 0.1 mol/L DTT, and 0.1 mol/L Tris-HCl (pH 8.5) was incubated at 40° C. for 3 hours. The refolding buffer was 0.1 mol/L Tris-HCl buffer at a pH of 8.5, containing 1.0 mol/L urea, 0.0054 mol/L cystamine, 0.025 or 0.05 mol/L NaCl and 0.001 mol/L EDTA-Na$_2$. In the experiment, the temperature of the thermostatic shaking bed was 25° C.

Activity Assay

Lysozyme activity was assayed with *Micrococcus lysodeikticus* as a substrate. In the assay, 1.30 ml of substrate in phosphate buffer (pH 6.2) with a concentration of 0.25 mg/ml was mixed thoroughly with 0.10 ml diluted protein refolding buffer, and the variation of absorbency of the reaction solution was measured at 450 nm. The assaying of the variation was conducted at a temperature of 25° C. The enzyme activity was estimated by the ratio absorbance decrease in the initial 90 s of refolded lysozyme and that of native enzyme. In the refolding method of the invention, the final concentrations of the resin in the refolding were 0 and 0.2 g/ml, respectively.

Refolded Protein Collection

After refolding, the supernatant was collected by gravity settlement for 5 minutes. Then, 0.3 ml refolding buffer was added to wash the resin. After that, the supernatant further obtained was collected by centrifugation at 10000 rpm for 1 minute. In order to make sure that the refolded protein was completely collected, the settled resin was washed five times finally. The pooled supernatant was used for further analysis.

Results

Figure 3:
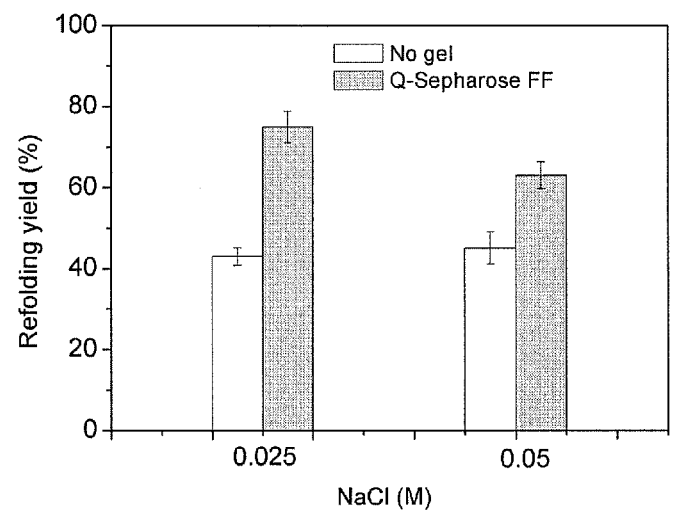
FIG. 3 illustrates the strong anion-exchange resin, Q-Sepharose FF, facilitates refolding of denatured and reduced lysozyme at 4 mg/ml in the presence of NaCl.

The variations of refolding yield in terms of time in the presence and absence of the anion-exchange resin after refolding for four hours are illustrated in FIG. 3. The result indicated that the application of the anion-exchange resin, Q-Sepharose Fast Flow, as the additive could significantly improve the refolding yield of denatured and reduced lysozyme. Even the protein concentration was 4 mg/ml, the refolding yield of lysozyme could also achieve 75% in the presence of 0.025 mol/L NaCl and 63% in the presence of 0.05 mol/L NaCl. However, the refolding yield of lysozyme was only 45% in the absence of the resin.

Recovery of Ion Exchange Resins

After the refolding, the settled Q-Sepharose Fast Flow was equilibrated with 1 mol/L NaCl solution for 10 minutes, and then the mixture was centrifuged at 10000 rpm for 1 minute to remove adsorbed impurities in the supernatant. After that, the resin was transferred into a sintered glass filter funnel and washed six times with 16 ml NaCl solution at the concentration of 0.5 mol/L. Finally, the resin was further washed six times with 16 ml deionized water, and stored in ethanol solution with a concentration of 20%.

Example 4

Strong anion-exchange resin, Q-Sepharose Fast Flow at 0.025 g/ml and 0.5 g/ml, facilitates the refolding of the denatured and reduced lysozyme.

Ion-Exchange Resin Preparation

The anion-exchange resin was the Q-Sepharose Fast Flow mentioned in EXAMPLE 1 of this invention.

Preparation of Denatured and Reduced Protein

In preparation of denatured and reduced protein, 60 mg/ml lysozyme in denatured and reduced buffer containing 8 mol/L urea, 0.1 mol/L DTT, and 0.1 mol/L Tris-HCl (pH 8.5) was incubated at 40° C. for 3 hours. The refolding buffer was 0.1 mol/L Tris-HCl buffer at a pH of 8.5, containing 1.0 mol/L urea, 0.0054 mol/L cystamine, and 0.001 mol/L EDTA-Na$_2$. In the experiment, the temperature of the thermostatic shaking bath in the course of experiment was 25° C.

Activity Assay

Lysozyme activity was assayed with *Micrococcus lysodeilaicus* as a substrate. In the assay, 1.30 ml of substrate in phosphate buffer (pH 6.2) with a concentration of 0.25 mg/ml was mixed thoroughly with 0.10 ml diluted protein refolding buffer, and the variation of absorbency of the reaction solution was measured at 450 nm. The assaying of the variation was conducted at a temperature of 25° C. The enzyme activity was estimated by the ratio of absorbance decrease in the initial 90 s of the refolded lysozyme to that of native enzyme. In the refolding method of the invention, the final concentrations of the resin in the refolding were 0, 0.025 g/ml and 0.5 g/ml, respectively.

Refolded Protein Collection

After refolding in the presence of the resin, the supernatant was collected by gravity settlement for 5 minutes. And then 0.075 ml and 1.0 ml refolding buffer were respectively added to wash the resin. After that, the supernatant was collected by centrifugation at 10000 rpm for 1 minute. In order to make sure that the refolded protein was completely collected, the settled resin was washed five times finally.

Results

Figure 4:
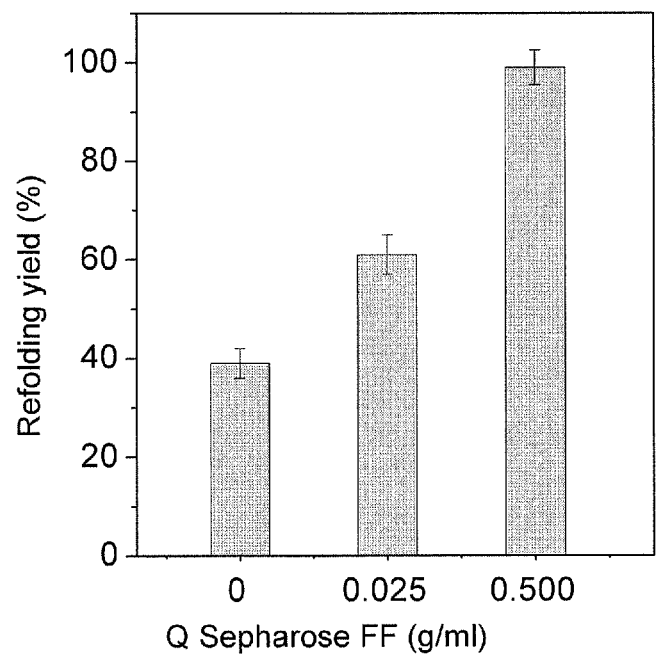
FIG. 4 illustrates the refolding of denatured and reduced lysozyme facilitated by the strong anion-exchange resin, Q-Sepharose FF, at concentrations of 0, 0.025 and 0.5 g/ml.

The variations of refolding yield in terms of time in the presence and absence of the anion-exchange resin after refolding for four hours are illustrated in FIG. 4. When the other conditions were the same, the result indicated that the application of the anion-exchange resin, Q-Sepharose Fast Flow, as the additive could significantly improve the refolding yield of denatured and reduced lysozyme. Even the anion-exchange resin was at a low concentration, a high refolding yield of lysozyme could also be achieved. When the protein concentration was 4 mg/ml, the refolding yield of lysozyme was only 40%; however, it reached 60% in the presence of 0.025 g/ml resin, and approached 100% in the presence of 0.5 g/ml resin.

Recovery of Ion Exchange Resins

After the refolding, the settled Q-Sepharose Fast Flow was equilibrated with 1 mol/L NaCl solution for 10 minutes, and then the mixture was centrifuged at 10000 rpm for 1 minute to remove adsorbed impurities in the supernatant. After that, the resin was transferred into a sintered glass filter funnel and washed six times with 16 ml NaCl solution at the concentration of 0.5 mol/L. Finally, the resin was further washed six times with 16 ml deionized water, and stored in ethanol solution with a concentration of 20%.

Example 5

Strong anion-exchange resin, Q-Sepharose Fast Flow, facilitates the refolding of the denatured and reduced lysozyme at a concentration of 0.07 g/ml.

Ion-Exchange Resin Preparation

The anion-exchange resin was the Q-Sepharose Fast Flow mentioned in EXAMPLE 1 of this invention.

Preparation of Denatured and Reduced Protein

In preparation of denatured and reduced protein, 14.3 mg/ml lysozyme in denatured and reduced buffer containing 8 mol/L urea, 0.1 mol/L DTT, and 0.1 mol/L Tris-HCl (pH 8.5) was incubated at 40° C. for 3 hours. The refolding buffer was 0.1 mol/L Tris-HCl buffer at a pH of 8.5, containing 2.0 mol/L urea, 0.0005 mol/L cystamine, and 0.001 mol/L EDTA-$Na_2$. In the experiment, the temperature of the thermostatic shaking bed was 25° C.

Activity Assay

Lysozyme activity was assayed with *Micrococcus lysodeikticus* as a substrate. In the assay, 1.30 ml of substrate in phosphate buffer (pH 6.2) with a concentration of 0.25 mg/ml was mixed thoroughly with 0.10 ml diluted protein refolding buffer, and the variation of absorbency of the reaction solution was measured at 450 nm. The assaying of the variation was conducted at a temperature of 25° C. The enzyme activity was estimated by the ratio absorbance decrease in the initial 90 s of the refolded lysozyme and that of native enzyme. In the refolding method of the invention, the final concentrations of the resin in the refolding were 0 and 0.2 g/ml, respectively.

Refolded Protein Collection

After refolding, the supernatant was collected by gravity settlement for 5 minutes. Then, 0.4 ml refolding buffer were added to wash the settled resin. After that, the supernatant was collected by centrifugation at 10000 rpm for 1 minute. In order to make sure that the refolded protein was completely collected, the settled resin was washed five times finally.

Results

Figure 5:
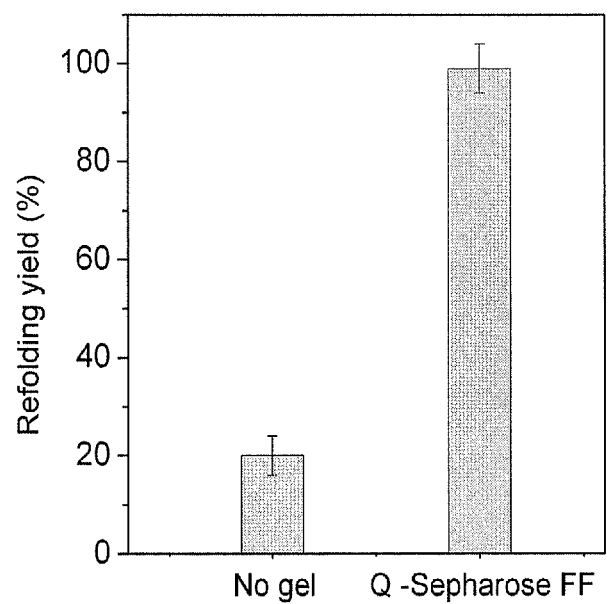
FIG. 5 illustrates the refolding of denatured and reduced lysozyme at 0.07 mg/ml in the presence and absence of Q-Sepharose FF.

The variations of refolding yield in terms of time in the presence and absence of the anion-exchange resin after refolding for three hours are illustrated in FIG. 5. The result indicated that the application of the anion-exchange resin, Q-Sepharose Fast Flow at a concentration of 0.2 g/ml, as the additive could significantly improve the refolding yield of denatured and reduced lysozyme. When the protein concentration was 0.07 mg/ml, the refolding yield of lysozyme could approach 100%, but it could be only 20% in the absence of the resin.

Recovery of Ion Exchange Resins

After the refolding, the settled Q-Sepharose Fast Flow was equilibrated with 1 mol/L NaCl solution for 10 minutes, and then the mixture was centrifuged at 10000 rpm for 1 minute to remove adsorbed impurities in the supernatant. After that, the resin was transferred into a sintered glass filter funnel and washed six times with 16 ml NaCl solution at the concentration of 0.5 mol/L. Finally, the resin was further washed six times with 16 ml deionized water, and stored in ethanol solution with a concentration of 20%.

Example 6

Strong anion-exchange resin, Q-Sepharose Fast Flow, facilitates the refolding of the denatured and reduced lysozyme at a concentration of 4 mg/ml.

Ion-Exchange Resin Preparation

The anion-exchange resin in this example was the Q-Sepharose Fast Flow. 2 ml such resin stored in ethanol solution with a concentration of 20% was placed in a sintered glass filter funnel, 20% of the ethanol solution was drained by suction, and then the resin was washed four times with 160 ml NaCl solution with a concentration of 0.5 mol/L. In each washing cycle, 40 ml said NaCl solution was added, and the mixture was stirred thoroughly with a glass stick; after that, the solution was drained by suction. The resin was further washed five times with 200 ml deionized water, and in each of these washing cycles, 40 ml deionized water was added and the mixture was stirred thoroughly; and then the solution was drained by suction; finally, the resin was washed with deionized water, and the water solution was drained by suction for 10 minutes and then the resin was stored in a refrigerator at 4° C.

Preparation of Denatured and Reduced Protein

In preparation of denatured and reduced protein, the 60 mg/ml lysozyme in denatured and reduced buffer containing 8 mol/L urea, 0.1 mol/L DTT, 0.001 mol/L EDTA-$Na_2$ and 0.1 mol/L Tris-HCl (pH 8.5) was incubated at 40° C. for 3 hours. The refolding buffer was 0.1 mol/L Tris-HCl buffer at a pH of 8.5, containing 2.0 mol/L urea, 0.0054 mol/L glutathion (GSSG), and 0.001 mol/L EDTA-$Na_2$. In the absence of the resin, the refolding buffer was incubated at 20° C. until the temperature of the buffer stable. In the presence of the resin, 0.2 g of the resin was added into the refolding buffer to prepare 1.0 ml of the mixture, and then the mixture was incubated at 20° C. until the temperature of the mixture stable. Then, the denatured protein was added to the refolding buffer, and thoroughly mixed. After that, the mixture was put on the thermostatic shaking bed for refolding at 20° C. and 170 rpm.

Activity Assay

Lysozyme activity was assayed with *Micrococcus lysodeikticus* as a substrate. In the assay, 1.30 ml of substrate in phosphate buffer (pH 6.2) with a concentration of 0.25 mg/ml was mixed thoroughly with 0.10 ml diluted protein refolding buffer, and the variation of absorbency of the reaction solution was measured at 450 nm. The assaying of the variation was conducted at a temperature of 25° C. The enzyme activity was estimated by the ratio absorbance decrease in the initial 90 s of the refolded lysozyme to that of native enzyme.

Refolded Protein Collection

After refolding, the supernatant was collected by centrifugation at 10000 rpm for 1 minute. Then, 0.4 ml refolding buffer was added to wash the settled resin. After that, the supernatant further obtained was collected by centrifugation. In order to make sure that the refolded protein was completely collected, the settled resin was washed four times finally.

Results

Figure 6:
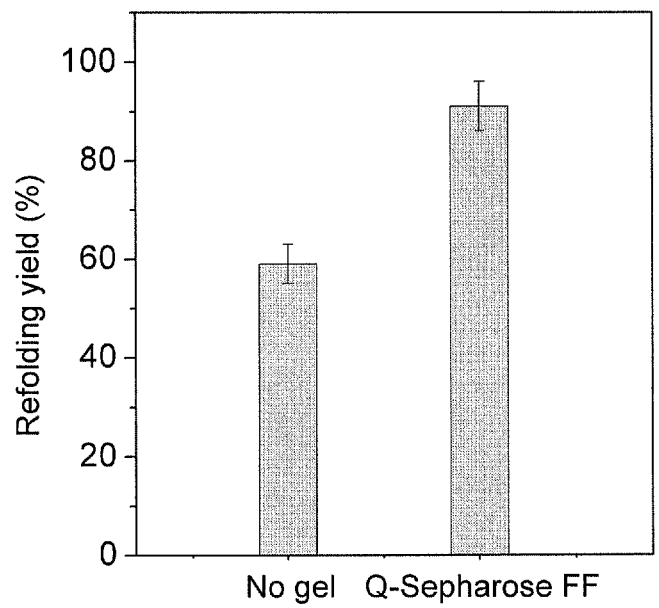
FIG. 6 illustrates the refolding of denatured and reduced lysozyme at 4 mg/ml in the presence and absence of Q-Sepharose FF, wherein the oxidant in the refolding system is glutathione (GSSG).

The variations of refolding yield in the presence and absence of the anion-exchange resin after three hours are illustrated in FIG. 6. The result indicated that the application of the anion-exchange resin, such as Q-Sepharose Fast Flow, as the additive could significantly improve the refolding yield of denatured and reduced lysozyme that is positively charged in the presence of GSSG as oxidant. The refolding yield of lysozyme could achieve 91%, even the protein concentration was 4 mg/ml. However, the refolding yield of lysozyme was only 59% in the absence of the resin.

Recovery of the Ion Exchange Resin

After the refolding, 0.2 g Q-Sepharose Fast Flow was equilibrated with 0.5 mol/L NaCl solution for 15 minutes, and then the mixture was centrifuged at 10000 rpm for 1 minute to remove adsorbed impurities in the supernatant. After that, the resin was transferred into a sintered glass filter funnel and washed four times with 16 ml NaCl solution at a concentration of 1 mol/L. Finally, the resin was further washed four times with 16 ml deionized water, and stored in ethanol solution with a concentration of 20%.

Example 7

Strong cation-exchange resin, SP-Sepharose Fast Flow, facilitates refolding of denatured and reduced Bovine Serum Albumin (BSA) at a protein concentration of 2 mg/ml.

Ion-Exchange Resin Preparation

As BSA carries negative charges at pH 9, a negatively charged cation-exchange resin, SP-Sepharose Fast Flow, was chosen to facilitate BSA refolding. After 2 ml said ion exchange resin stored in ethanol solution with a concentration of 20% was transferred into a sintered glass filter funnel, 20% of said ethanol solution was drained by suction, and then the resin was washed eight times with 400 ml NaCl solution with a concentration of 0.2 mol/L. Wherein, in each washing cycle, 50 ml said NaCl solution was added, and the mixture was stirred thoroughly with a glass stick and after that the water solution was drained by suction. The resin was further washed eight times with 400 ml deionized water, and in each of these washing cycles, 50 ml deionized water was added and the mixture was stirred thoroughly; and then the solution was drained by suction; Finally, the resin was washed with deionized water, and the water solution was drained by suction for 10 minutes and then the resin was stored in a refrigerator at 4° C.

Preparation of Denatured and Reduced Protein

In preparation of denatured and reduced protein, 60 mg/ml BSA in denatured and reduced buffer containing 8 mol/L urea, 0.1 mol/L DTT, 0.001 mol/L EDTA-$Na_2$ and 0.05 mol/L Tris-HCl (pH 8.5) was incubated at 25° C. for 3 hours. The refolding buffer was 0.05 mol/L Tris-HCl buffer at a pH of 9, containing 0.0027 mol/L cystamine, and 0.001 mol/L EDTA-$Na_2$. In the absence of the resin, 2 ml of the refolding buffer was incubated at 25° C. until the temperature of the buffer stable. In the presence of the resin, 0.2 g of the resin was added into the refolding buffer to prepare 2.0 ml of the mixture, and then the mixture was incubated at 25° C. until the temperature of the mixture stable. Then, the denatured protein was added to the refolding buffer, and thoroughly mixed. After that, the mixture was put on the thermostatic shaking bath for refolding at 25° C. and 100 rpm.

Activity Assay

The natural BSA in the refolding buffer was separated by Revised-Phase chromatography (RP-HPLC) through C18, and quantitatively determined by the peak area. In the method of refolding of this invention, the final concentration of the resin in the refolding was 0.1 g/ml.

Refolded Protein Collection

After refolding, the supernatant was collected by gravity settlement for 15 minutes. Then, 0.3 ml refolding buffer was added to wash the settled resin. After that, the supernatant was removed by centrifugation at 10000 rpm for 1 minute, and the resin was further washed twice in terms of this method finally.

Result

Figure 7:
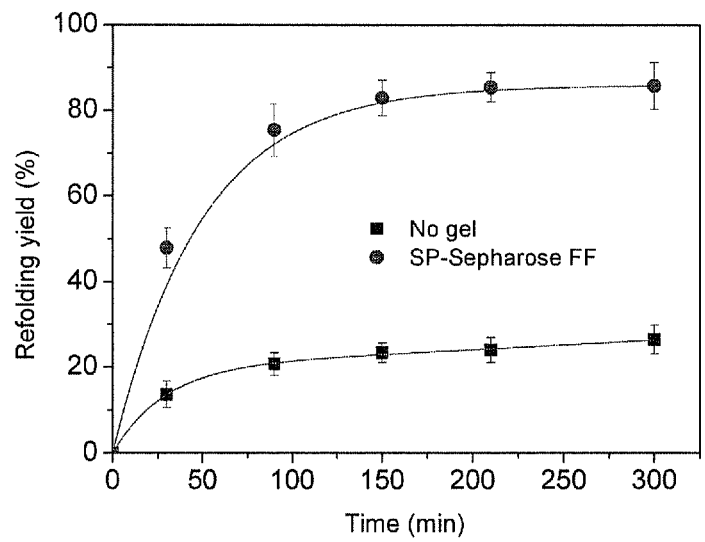
FIG. 7 illustrates the strong cation-exchange resin, SP-Sepharose Fast Flow (SP-Sepharose FF), facilitates refolding of reduced and denatured bovine serum albumin (BSA) at 2 mg/ml.

The variations of refolding yield in terms of time in the presence and absence of the cation-exchange resin are illustrated in FIG. 7. The result indicated that the application of the cation-exchange resin, such as SP-Sepharose Fast Flow, as the additive could significantly improve the refolding yield of denatured and reduced Bovine Serum Albumin (BSA) that is negatively charged. The refolding yield of BSA could achieve 85%, even the protein concentration was 2 mg/ml. However, the refolding yield of BSA was only 26% in the absence of the resin.

Recovery of Cation-Exchange Resin

After the refolding, the settled SP-Sepharose Fast Flow was equilibrated with 2 mol/L NaCl solution for 15 minutes, and then the mixture was centrifuged at 10000 rpm for 1 minute to remove adsorbed impurities in the supernatant. After that, the resin was transferred into a sintered glass filter funnel and washed five times with 16 ml NaCl solution at the concentration of 0.5 mol/L. Finally, the resin was further washed five times with 16 ml deionized water, and stored in ethanol solution with a concentration of 20%.

Example 8

Weak cation-exchange resin, CM-Sepharose Fast Flow, facilitates refolding of denatured and reduced bovine serum albumin (BSA) at a protein concentration of 2 mg/ml.

Ion-Exchange Resin Preparation

A cation-exchange resin, CM-Sepharose Fast Flow, was chosen to facilitate BSA refolding. After 2 ml said ion exchange resin stored in ethanol solution with a concentration of 20% was transferred into a sintered glass filter funnel, 20% of said ethanol solution was drained by suction, and then the resin was washed four times with 160 ml NaCl solution with a concentration of 0.5 mol/L. Wherein, in each washing cycle, 40 ml said NaCl solution was added, and the mixture was stirred thoroughly with a glass stick and after that the water solution was drained by suction. After, that, the resin was washed five times with 200 ml deionized water, and in each washing cycle, 40 ml said deionized water was added, and the mixture was stirred thoroughly with a glass stick. Finally, the water solution was drained by suction for 10 minutes and the resin stored in a refrigerator at 4° C.

Preparation of Denatured and Reduced Protein

In preparation of denatured and reduced protein, 60 mg/ml BSA in denatured and reduced buffer containing 8 mol/L urea, 0.1 mol/L DTT, 0.001 mol/L EDTA-$Na_2$ and 0.05 mol/L Tris-HCl (pH 8.5) was incubated at 25° C. for 3 hours. The refolding buffer was 0.05 mol/L Tris-HCl buffer at a pH of 9, containing 0.0027 mol/L cystamine, and 0.001 mol/L EDTA-$Na_2$. In the absence of the resin, 2 ml of the refolding buffer was incubated at 25° C. until the temperature of the buffer stable. In the presence of the resin, 0.2 g of the resin was added into the refolding buffer to prepare 2.0 ml of the mixture, and then the mixture was incubated at 25° C. until the temperature of the mixture stable. Then, the denatured protein was added to the refolding buffer, and thoroughly mixed. After that, the mixture was put on the thermostatic shaking bath for refolding at 25° C. and 100 rpm.

Activity Assay

The native BSA in the refolding buffer was separated by Revised-Phase chromatography (RP-HPLC) through C18, and quantitatively determined by the peak area. In the method of refolding of this invention, the final concentration of resin in the refolding was 0.1 g/ml.

Refolded Protein Collection

After refolding, the supernatant was collected by centrifugation at 10000 rpm for 1 minute, and then 0.3 ml refolding buffer was added to wash the resin settled, after that, the supernatant was removed by centrifugation at 10000 rpm for 1 minute, and the resin was further washed twice in terms of this method. Finally, the yield of the refolded protein approached to 100%.

Result

Figure 8:
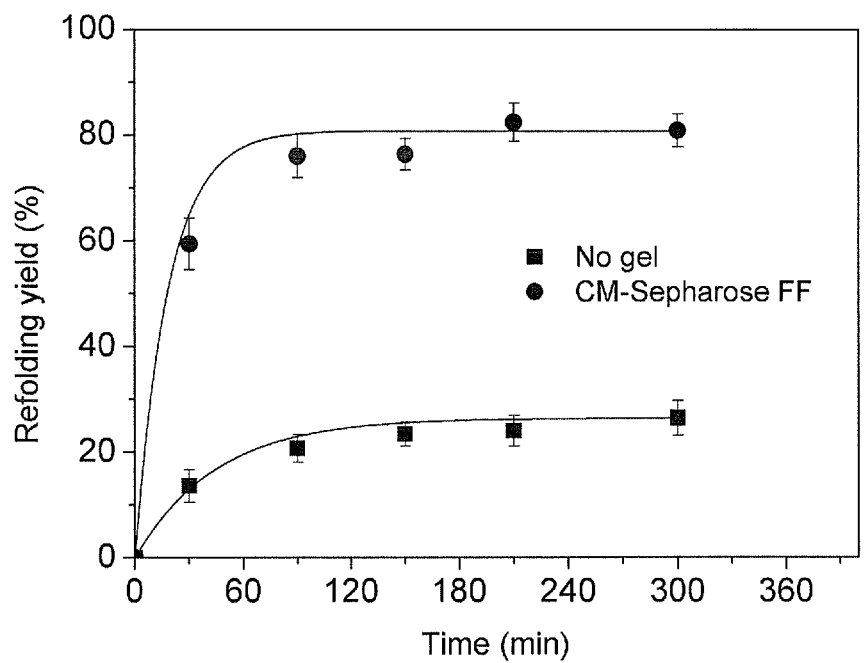
FIG. 8 illustrates the weak cation-exchange resin, CM-Sepharose Fast Flow (CM-Sepharose FF), facilitates refolding of reduced and denatured BSA at 2 mg/ml.

The variations of refolding yield in terms of time in the presence and absence of the cation-exchange resin are illustrated in FIG. 8. The result indicated that the application of the cation-exchange resin, such as CM-Sepharose Fast Flow, as the additive could significantly improve the refolding yield of denatured and reduced Bovine Serum Albumin (BSA) that is negatively charged. The refolding yield of BSA could achieve 82%, even the protein concentration was 2 mg/ml. However, the refolding yield of BSA was only 26% in the absence of the resin.

Example 9

Strong cation-exchange resin, SP-Sepharose Fast Flow, facilitates refolding of denatured carbonic anhydrase II (CAII) with a concentration of 0.4 mg/ml.

Preparation of the Ion Exchange Resin

As CAII carries negative charges at pH 7.5, a negatively charged ion exchange resins, SP-Sepharose Fast Flow, which was prepared as in EXAMPLE 7, was chosen.

Preparation of Denatured and Reduced Protein

The denatured and reduced protein was prepared by incubating CAII solution with a concentration of 12 mg/ml in the denatured buffer containing 8 mol/L urea, and 0.05 mol/L Tris-HCl (pH 7.5) for 24 hours at 25° C.

Refolding

The refolding buffer was 0.05 mol/ml Tris-HCl at a pH of 7.5, containing 2 mol/ml urea. In the absence of the resin, 2 ml of the refolding buffer was incubated at 25° C. until the temperature of the buffer stable. In the presence of the resin, 0.2 g of the resin was added into the refolding buffer to prepare 2.0 ml of the mixture, and then the mixture was incubated at 25° C. until the temperature of the mixture stable. Then, the abovementioned denatured protein was added to the refolding buffer, and thoroughly mixed. After that, the mixture was put on the thermostatic shaking bath for refolding at 25° C. and 170 rpm.

Activity Assay

The recovery of CAII was assayed through hydration reaction with p-nitrophenyl acetate (pNPA) as the substrate. 15 μl said denatured and reduced protein was added to 1 ml said refolding buffer at a pH of 7.5 containing 0.05 mol/L Tris-HCl and 0.005 mol/L EDTA-$Na_2$ and 10 μl pNPA acetonitrile solution with a pNPA concentration of 0.1 mol/L. The variation of absorbency of the reaction solution was measured at 400 nm. The assaying of the variation was conducted at a temperature of 25° C. The enzyme activity of CAII was estimated by the ratio of absorbance increase in the initial 90 s of refolded CAII to that of native enzyme. In the method of refolding of this invention, the final concentration of the resin in the refolding was 0.1 g/ml.

Refolded Protein Collection

After refolding, the supernatant was collected by gravity settlement for 10 minutes, and then 0.3 ml refolding buffer was added to wash the resin; after that, the supernatant was removed by centrifugation at 10000 rpm for 1 minute, and the resin was further washed twice in terms of this method. Finally, the yield of the refolded protein approached 100%.

Result

Figure 9:
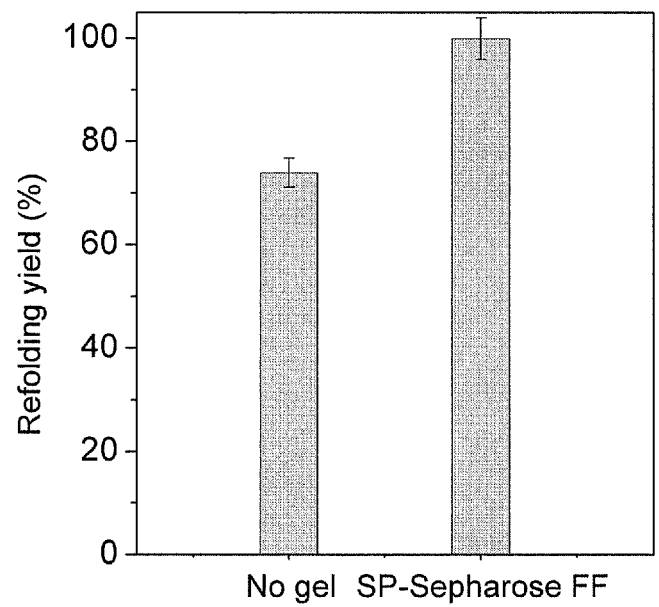
FIG. 9 illustrates the strong cation-exchange resin, SP-Sepharose FF, facilitates the refolding of denatured carbonic anhydrase II (CAII) at 0.4 mg/ml.

After 4 hours, the variations of refolding yield in the presence and absence of the cation-exchange resin are illustrated in FIG. 9. When the other conditions were the same, the result indicated that the application of the cation-exchange resin, such as SP-Sepharose Fast Flow, as the additive could significantly improve the refolding yield of denatured and reduced CAII. The refolding yield could approach 100%, even the protein concentration was 0.4 mg/ml. However, the refolding yield of CAII was only 74% in the absence of the resin.

Example 10

Weak cation-exchange resin, CM-Sepharose Fast Flow, facilitates refolding of denatured carbonic anhydrase II (CAII) with a concentration of 0.4 mg/ml.

Ion-Exchange Resin Preparation

As CAII carries negative charges at pH 7.5, a negatively charged ion exchange resin, CM-Sepharose Fast Flow, which was prepared as in the EXAMPLE 8, was chosen.

Preparation of Denatured and Reduced Protein

The denatured and reduced protein was prepared by incubating CAII solution with a concentration of 12 mg/ml in the denatured buffer containing 8 mol/L urea, and 0.05 mol/L Tris-HCl (pH 7.5) for 24 hours at 25° C.

Refolding

The refolding buffer was 0.05 mol/ml Tris-HCl buffer at a pH of 7.5, containing 2 mol/mi urea. In the absence of the resin, 2 ml of the refolding buffer was incubated at 25° C. until the temperature of the buffer stable. In the presence of the resin, 0.2 g of the resin was added into the refolding buffer to prepare 2.0 ml of the mixture, and then the mixture was incubated at 25° C. until the temperature of the mixture stable. Then, the abovementioned denatured protein was added to the refolding buffer, and thoroughly mixed. After that, the mixture was put on the thermostatic shaking bath for refolding at 250 and 170 rpm.

Activity Assay

The recovery of CAII was assayed through hydration reaction with p-nitrophenyl acetate (pNPA) as the substrate. 15 μl said denatured and reduced protein was added to 1 ml said refolding buffer at a pH of 7.5 containing 0.05 mol/L Tris-HCl and 0.005 mol/L EDTA-$Na_2$ and 10 μL pNPA acetonitrile solution with a pNPA concentration of 0.1 mol/L. The variation of absorbency of the reaction solution was measured at 400 nm. The assaying of the variation was conducted at a temperature of 25° C. The enzyme activity of CAII was estimated by the ratio of absorbance increase in the initial 90 s of refolded CAII to native enzyme. In the method of refolding of this invention, the final concentration of the resin in the refolding buffer was 0.1 g/ml.

Refolded Protein Collection

After refolding, the supernatant was collected by gravity settlement for 5 minutes, and then 0.3 ml refolding buffer was added to wash the resin; after that, the supernatant was removed by centrifugation at 10000 rpm for 1 minute, and the resin was further washed twice in terms of this method. Finally, the yield of the refolded protein approached 100%.

Result

Figure 10:
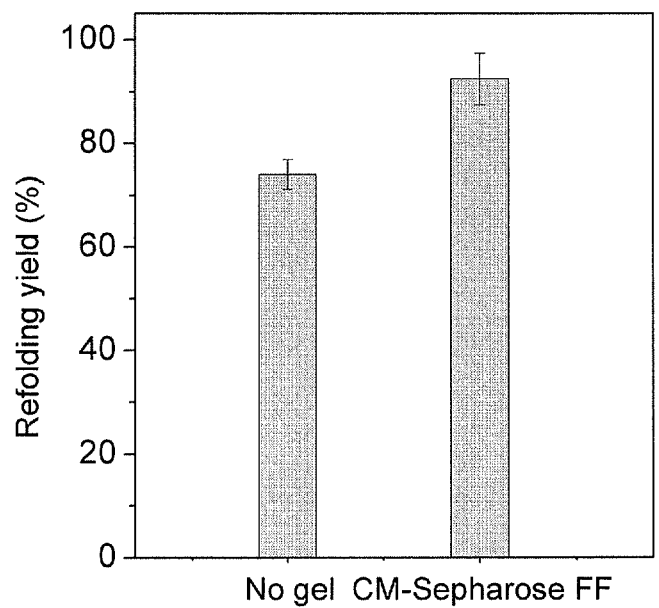
FIG. 10 illustrates the weak cation-exchange resin, CM-Sepharose FF, facilitates the refolding of denatured CAII at 0.4 mg/ml.

After 4 hours, the variations of refolding yield in the presence and absence of the anion-exchange resin are illustrated in FIG. 10. When the other conditions were the same, the result indicated that the application of the cation-exchange resin, such as CM-Sepharose Fast Flow, as the additive could significantly improve the refolding yield of denatured and reduced CAII. The refolding yield could approach 92%, even the protein concentration was 0.4 mg/ml. However, the refolding yield of CAII was only 74% in the absence of the resin.

While this invention has been described as having several preferred embodiments, the present invention can be further modified within the spirit and scope of this disclosure. This application is therefore intended to cover any variations, uses, or adaptations of the invention using its general principles. Further, this application is intended to cover such departures from this present disclosure as come within known or customary practice in the art to which this invention pertains and which fall within the limits of the appended claims.

The invention claimed is:

1. A method for protein refolding with an ion exchange resin as an additive, comprising the following steps:
   a. choosing an ion exchange resin that comprises charged groups with the same sign as a net charge of a denatured protein to be refolded;
   b. removing heterogeneous ions from the ion exchange resin by washing the ion exchange resin sequentially with saline solution and deionized water, to prepare the ion exchange resin;
   c. mixing the ion exchange resin with a refolding buffer thoroughly, then adding the denatured protein to the refolding buffer and allowing the denatured protein to refold; and
   d. after step c, collecting the supernatant by centrifugation or settlement, to obtain a solution containing the refolded protein.

2. The method of claim 1, wherein the ion exchange resin is a positively charged anion-exchange resin or a negatively charged cation-exchange resin.

3. The method of claim 1, wherein the ion exchange resin is a positively charged anion-exchange resin selected from DEAE-Sepharose Fast Flow and Q-Sepharose Fast Flow.

4. The method of claim 1, wherein the ion exchange resin is a negatively charged cation-exchange resin selected from SP-Sepharose Fast Flow and CM-Sepharose Fast Flow.

5. The method of claim 1, wherein the refolding buffer contains 0.02-0.1 mol/L Tris, 0-0.003 mol/L ethylenediaminetetraacetic acid disodium (EDTA-$Na_2$), and 0-2 mol/L urea, and the pH value of the refolding buffer is 7.5-9.0.

6. The method of claim 4, wherein the refolding buffer contains inorganic salt, and a concentration of the inorganic salt is not greater than 0.05 mol/L.

7. The method of claim 1, wherein step b further comprises the following sub-steps:
   transferring the ion exchange resin into a sintered glass filter funnel so as to drain the liquid by suction; and then
   washing the resin 3-8 times successively with 0.2-2 mol/L NaCl solution and deionized water;
   wherein a volume of NaCl solution and deionized water in each washing cycle is 20-30 times as that of the resin.

8. The method of claim 1, wherein in step c,
   a concentration of the ion exchange resin in the refolding buffer is 0.025-0.5 g/ml;
   the mixture of ion exchange resin and refolding buffer is put in a thermostatic water bath at a temperature of 20-37° C., and shaken to be pre-equilibrated until the temperature of the mixture is stable; then
   the protein to be refolded is added, and a final concentration of the protein in the refolding buffer is 0.07-4 mg/ml; and
   after being thoroughly mixed, the mixture is put into the thermostatic water bath and shaken at 50-170 rpm for refolding, wherein, the temperature for refolding is the same as that for pre-equilibration.

9. The method of claim 1, wherein the denatured protein is an aggregation-prone protein with or without disulfide bonds.

10. The method of claim 5, wherein the refolding buffer contains inorganic salt, and a concentration of the inorganic salt is not greater than 0.05 mol/L.

* * * * *